United States Patent [19]

Gleason et al.

[11] Patent Number: 4,954,513

[45] Date of Patent: Sep. 4, 1990

[54] LEUKOTRIENE ANTAGONISTS

[75] Inventors: John G. Gleason, Downingtown; Ralph F. Hall, Villanova; Joanne Smallheer, Landenberg, all of Pa.

[73] Assignee: SmithKline Beecham Corporation, Philadelphia, Pa.

[21] Appl. No.: 288,827

[22] Filed: Dec. 23, 1988

[51] Int. Cl.$^5$ .................. A61K 31/18; C07C 143/74; C07C 143/80

[52] U.S. Cl. ........................... 514/381; 514/538; 514/539; 514/542; 514/562; 514/604; 514/605; 548/253; 560/12; 560/13; 562/430; 564/82

[58] Field of Search .................. 560/12, 13; 562/430; 564/82; 548/253; 514/381, 539, 542, 538, 562, 604, 605

[56] References Cited

U.S. PATENT DOCUMENTS

| 66,588 | 6/1987 | Frazee et al. . |
| 66,592 | 6/1987 | Gleason et al. . |
| 4,609,744 | 9/1986 | Young et al. . |

FOREIGN PATENT DOCUMENTS

| 68739 | 1/1983 | European Pat. Off. . |
| 104885 | 4/1984 | European Pat. Off. . |
| 108592 | 5/1984 | European Pat. Off. . |
| 123543 | 10/1984 | European Pat. Off. . |
| 132366 | 1/1985 | European Pat. Off. . |
| 132367 | 1/1985 | European Pat. Off. . |
| 190042 | 8/1986 | European Pat. Off. . |
| 186426 | 9/1986 | European Pat. Off. . |
| 202759 | 11/1986 | European Pat. Off. . |
| 2746754 | 4/1978 | Fed. Rep. of Germany . |
| 1397647 | 6/1975 | United Kingdom . |
| 2144422A | 3/1985 | United Kingdom . |
| 2184121 | 6/1987 | United Kingdom . |

OTHER PUBLICATIONS

Chemical Abstracts, vol. 101, No. 17, p. 718, Abstract 151857q (Oct. 22, 1984).
Patent Abstracts of Japan, vol. 9, No. 306 (C-317) (2029) Dec. 3, 1985.
Derwent Patent Abstract 84-014267/03 of Japanese Patent Application 58206556A published Dec. 1, 1983.
Chemical Abstracts 96(17):143290n.
Chemical Abstracts 94(9):64755y.
Chemical Abstracts, vol. 96, 98909h (1982).
Gleason et al., *J. Med. Chem.*, 30, 6, 959–961 (1987).

*Primary Examiner*—Michael L. Shippen
*Attorney, Agent, or Firm*—James M. Kanagy; Stuart R. Suter; Edward T. Lentz

[57] ABSTRACT

This invention relates to alkanoic acid compounds having phenyl and heteroarylthio substituents which are useful as leukotriene antagonists, pharmaceutical compositions containing such compounds, and methods of treating diseases in which leukotrienes are a factor by administration of an effective amount of the above compounds or compositions.

14 Claims, No Drawings

LEUKOTRIENE ANTAGONISTS

BACKGROUND OF THE INVENTION

"Slow Reacting Substance of Anaphylaxis" (SRS-A) has been shown to be a highly potent bronchoconstricting substance which is released primarily from mast cells and basophils on antigenic challenge. SRS A has been proposed as a primary mediator in human asthma. SRS A, in addition to its pronounced effects on lung tissue, also produces permeability changes in skin and may be involved in acute cutaneous allergic reactions. Further, SRS-A has been shown to effect depression of ventricular contraction and potentiation of the cardiovascular effects of histamine.

The discovery of the naturally occurring leukotrienes and their relationship to SRS-A has reinforced interest in SRS-A and other arachidonate metabolites. SRS-A derived from mouse, rat, guinea pig and man have all been characterized as mixtures of leukotriene-$C_4$ ($LTC_4$), leukotriene-$D_4$ ($LTD_4$) and leukotriene-$E_4$ ($LTE_4$), the structural formulae of which are represented below.

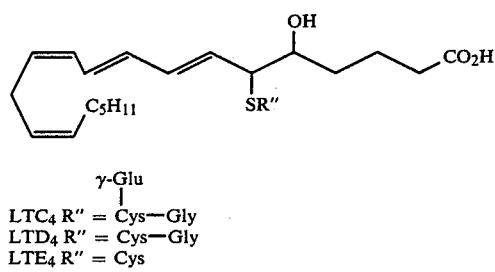

$LTC_4$ R" = Cys—Gly with γ-Glu
$LTD_4$ R" = Cys—Gly
$LTE_4$ R" = Cys

Leukotrienes are a group of eicosanoids formed from arachidonic acid metabolism via the lipoxygenase pathway. These lipid derivatives originate from $LTA_4$ and are of two types: (1) those containing a sulfido-peptide side chain ($LTC_4$, $LTD_4$, and $LTE_4$), and (2) those that are nonpeptidic ($LTB_4$) Leukotrienes comprise a group of naturally occurring substances that have the potential to contribute significantly to the pathogenesis of a variety of inflammatory and ischemic disorders. The pathophysiological role of leukotrienes has been the focus of recent intensive studies.

As summarized by Left, A. M., *Biochemical Pharmacology*, 35, 2, 123–127 (1986) both the peptide and nonpeptide leukotrienes exert microcirculatory actions, promoting leakage of fluid across the capillary endothelial membrane in most types of vascular beds. $LTB_4$ has potent chemotactic actions and contributes to the recruitment and adherence of mobile scavenger cells to the endothelial membrane. $LTC_4$, $LTD_4$ and $LTE_4$ stimulate a variety of types of muscles. $LTC_4$ and $LTD_4$ are potent bronchoconstrictors and effective stimulators of vascular smooth muscle. This vaso-constrictor effect has been shown to occur in pulmonary, coronary, cerebral, renal, and mesenteric vasculatures.

Leukotrienes have been implicated in a number of pulmonary diseases. Leukotrienes are known to be potent bronchoconstrictors in humans. $LTC_4$ and $LTD_4$ have been shown to be potent and selective peripheral airway agonists, being more active than histamine. [See Drazen, J. M. et al., *Proc. Nat'l. Acad. Sci. USA*, 77, 7, 4354–4358 (1980).] $LTC_4$ and $LTD_4$ have been shown to increase the release of mucus from human airways in vitro. [See Marom, Z. et al., *Am. Rev. Respir. Dis.*, 126, 449–451 (1982).] The leukotriene antagonists of the present invention can be useful in the treatment of allergic or non-allergic bronchial asthma or pulmonary anaphylaxis.

The presence of leukotrienes in the sputum of patients having cystic fibrosis, chronic bronchitis, and bronchiectasis at levels likely to have pathophysiological effects has been demonstrated by Zakrzewski et al. [See Zakrzewski, J. T. et al., *Prostaglandins*, 28, 5, 641 (1984).] Treatment of these diseases constitutes additional possible utility for leukotriene antagonists.

Leukotrienes have been identified in the nasal secretions of allergic subjects who underwent in vivo challenge with specific antigen. The release of the leukotrienes was correlated with typical allergic signs and symptoms. [See Creticos, P. S. et al., *New England J. of Med.*, 310, 25, 1626–1629 (1984).] This suggests that allergic rhinitis is another area of utility for leukotriene antagonists.

The role of leukotrienes and the specificity and selectivity of a particular leukotriene antagonist in an animal model of the adult respiratory distress syndrome was investigated by Snapper et al. [See Snapper, J. R. et al., *Abstracts of Int'l Conf. on Prostaglandins and Related Comp.*, Florence, Italy, p. 495 (June 1986).] Elevated concentrations of $LTD_4$ were shown in pulmonary edema fluid of patients with adult respiratory distress syndrome. [See Matthay, M. et al. *J. Clin. Immunol.*, 4, 479–483 (1981).] Markedly elevated leukotriene levels have been shown in the edema fluid of a patient with pulmonary edema after cardiopulmonary bypass. [See Swerdlow, B. N., et al., *Anesth. Analg.*, 65, 306–308, (1986).] LTC and LTD have also been shown to have a direct systemic arterial hypotensive effect and produce vasoconstriction and increased vasopermeability. [See Drazen et al., ibid.] This suggests leukotriene antagonists can also be useful in the areas of adult respiratory distress syndrome, pulmonary edema, and hypertension.

Leukotrienes have also been directly or indirectly implicated in a variety of non pulmonary diseases in the ocular, dermatologic, cardiovascular, renal, trauma, inflammatory, carcinogenic and other areas.

Further evidence of leukotrienes as mediators of allergic reactions is provided by the identification of leukotrienes in tear fluids from subjects following a conjunctival provocation test and in skin blister fluids after allergen challenge in allergic skin diseases and conjunctival mucosa. [See Bisgaard, H., et al., *Allergy*, 40, 417–423 (1985).] Leukotriene immunoreactivity has also been shown to be present in the aqueous humor of human patients with and without uveitis. The concentrations of leukotrienes were sufficiently high that these mediators were expected to contribute in a meaningful way to tissue responses. [See Parker, J. A. et al., Arch Ophthalmol, 104, 722–724 (1986).] It has also been demonstrated that psoriatic skin has elevated levels of leukotrienes. [See Ford Hutchinson, *J. Allergy Clin. Immunol.*, 74, 437–440 (1984).] Local effects of intracutaneous injections of synthetic leukotrienes in human skin were demonstrated by Soter et al. [See Soter et al. *J. Clin Invest Dermatol*, 80, 115–119 (1983).] Cutaneous vasodilation with edema formation and a neutrophil infiltrate were induced. Leukotriene synthesis inhibitors or leukotriene antagonists can also be useful in the treatment of ocular or dermatological diseases such as allergic conjunctivitis, uveitis, allergic dermatitis or psoriasis.

Another area of utility for leukotriene antagonists is in the treatment of cardiovascular diseases. Since peptide leukotrienes are potent coronary vasoconstrictors, they are implicated in a variety of cardiac disorders including arrhythmias, conduction blocks and cardiac depression. Synthetic leukotrienes have been shown to be powerful myocardial depressants, their effects consisting of a decrease in contractile force and coronary flow. The cardiac effects of $LTC_4$ and $LTD_4$ have been shown to be antagonized by a specific leukotriene antagonist, thus suggesting usefulness of leukotriene antagonists in the areas of myocardial depression and cardiac anaphylaxis. [See Burke, J. A., et al., *J. Pharmacology and Experimental Therapeutics*, 221, 1, 235–241 (1982).]

$LTC_4$ and $LTD_4$ have been measured in the body fluids of rats in endotoxic shock, but are rapidly cleared from the blood into the bile. Thus leukotrienes are formed in ischemia and shock. Specific inhibitors of leukotriene biosynthesis reduce the level of leukotrienes and therefore reduce manifestations of traumatic shock, endotoxic shock, and acute myocardial ischemia. Leukotriene receptor antagonists have also been shown to reduce manifestations of endotoxic shock and to reduce extension of infarct size. Administration of peptide leukotrienes has been shown to produce significant ischemia or shock. [See Lefer, A. M., *Biochemical Pharmacology*, 35, 2, 123–127 (1986).] Thus further areas of utility for leukotriene antagonists can be the treatment of myocardial ischemia, acute myocardial infarction, salvage of ischemic myocardium, angina, cardiac arrhythmias, shock and atherosclerosis.

Leukotriene antagonists can also be useful in the area of renal ischemia or renal failure. Badr et al. have shown that $LTC_4$ produces significant elevation of mean arterial pressure and reductions in cardiac output and renal blood flow, and that such effects can be abolished by a specific leukotriene antagonist. [See Badr, K. R. et al., *Circulation Research*, 54, 5, 492–499 (1984).] Leukotrienes have also been shown to have a role in endotoxin induced renal failure and the effects of the leukotrienes selectively antagonized in this model of renal injury. [See Badr, K. F., et al., *Kidney International*, 30, 474–480 (1986).] $LTD_4$ has been shown to produce local glomerular constrictor actions which are prevented by treatment with a leukotriene antagonist. [See Badr, K. F. et al., *Kidney International*, 29, 1, 328 (1986).] $LTC_4$ has been demonstrated to contract rat glomerular mesangial cells in culture and thereby effect intraglomerular actions to reduce filtration surface area. [See Dunn, M. J. et al., *Kidney International*, 27, 1, 256 (1985).] Thus another area of utility for leukotriene antagonists can be in the treatment of glomerulonephritis.

Leukotrienes have also been indicated in the area of transplant rejection. An increase in cardiac and renal allograft survival in the presence of a leukotriene receptor antagonist was documented by Foegh et al. [See Foegh, M. L. et al. *Advances in Prostaglandin, Thromboxane, and Leukotriene Research*, 13, 209–217 (1985).] Rejection of rat renal allografts was shown to produce increased amounts of $LTC_4$ [See Coffman, T. M. et al., *Kidney International*, 29, 1, 332 (1986).]

A further area of utility for leukotriene antagonists can be in treatment of tissue trauma, burns, or fractures. A significant increase in the production of cysteinyl leukotrienes was shown after mechanical or thermal trauma sufficient to induce tissue edema and circulatory and respiratory dysfunction. [See Denzlinger, C. et al., *Science*, 230, 330–332 (1985).]

Leukotrienes have also been shown to have a role in acute inflammatory actions. $LTC_4$ and $LTD_4$ have potent effects on vascular caliber and permeability and $LTB_4$ increases leukocyte adhesion to the endothelium. The arteriolar constriction, plasma leakage, and leukocyte adhesion bear close resemblance to the early events in acute inflammatory reactions. [See Dahlen, S. E. et al., *Proc. Natl. Acad. Sci. USA*, 78, 6, 3887–3891 (1981).] Mediation of local homeostasis and inflammation by leukotrienes and other mast cell-dependent compounds was also investigated by Lewis et al. [See Lewis, R. A. et al., *Nature*. 293, 103 108 (1981).] Leukotriene antagonists can therefore be useful in the treatment of inflammatory diseases including rheumatoid arthritis and gout.

Cysteinyl leukotrienes have also been shown to undergo enterohepatic circulation, and thus are indicated in the area of inflammatory liver disease. [See Denzlinger, C. et al., *Prostaglandins Leukotrienes and Medicine*, 21, 321–322 (1986).] Leukotrienes can also be important mediators of inflammation in inflammatory bowel disease. [See Peskar, B. M. et al., *Agents and Actions*, 18, 381–383 (1986).] Leukotriene antagonists thus can be useful in the treatment of inflammatory liver and bowel disease.

Leukotrienes have been shown to modulate IL-1 production by human monocytes [See Rola-Pleszczynski, M. et al., *J. of Immun.*, 135, 6, 3958–3961 (1985).] This suggests that leukotriene antagonists may play a role in IL 1 mediated functions of monocytes in inflammation and immune reactions.

$LTA_4$ has been shown to be a factor in inducing carcinogenic tumors and is considered a link between acute immunologic defense reactions and carcinogenesis. Leukotriene antagonists can therefore possibly have utility in treatment of some types of carcinogenic tumors. [See Wischnewsky, G. G. et al. *Anticancer Res.* 5, 6, 639 (1985).]

Leukotrienes have been implicated in gastric cytodestruction and gastric ulcers. Damage of gastro intestinal mucosa because of potent vasoconstriction and stasis of blood flow is correlated with increased levels of $LTC_4$. Functional antagonism of leukotriene effects may represent an alternative in treatment of mucosal injury. [See Dreyling, K. W. et al., *British J. Pharmacology*, 88, 236P (1986), and Peskar, B. M. et al. *Prostaglandins*, 31, 2, 283–293 (1986).] A leukotriene antagonist has been shown to protect against stress-induced gastric ulcer in rats. [See Ogle, C. W. et al., *IRCS Med. Sci.*, 14, 114–115 (1986).]

Other areas in which leukotriene antagonists can have utility because leukotrienes are indicated as mediators include prevention of premature labor [See Clayton, J. K. et al., *Proceedings of the BPS*, 573P, 17–19 Dec. 1984]; treatment of migraine headaches [See Gazzaniga, P. P. et al., Abstracts Int'l Conf. on Prostaglandins and Related Comp., 121, Florence, Italy (June 1986)]; and treatment of gallstones [See Doty, J. E. et al., *Amer. J. of Surgery*, 145, 54–61 (1983) and Marom, Z. et al., *Amer. Rev. Respir. Dis.*, 126, 449–451 (1982).

By antagonizing the effects of $LTC_4$, $LTD_4$ and $LTE_4$ or other pharmacologically active mediators at the end organ, for example, airway smooth muscle, the compounds and pharmaceutical compositions of the instant invention are valuable in the treatment of diseases in subjects, including human or animals, in which leukotrienes are a key factor.

SUMMARY OF THE INVENTION

This invention relates to compounds represented by structural formula (I)

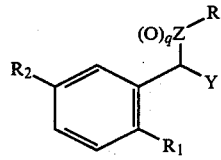

wherein:
Z is S or O;
q is 0 when Z is O and q is 0, 1 or 2 when Z is S;
R is $-(CH_2)_m COOH$, $-(CH_2)_m CO_2 R_3$, $-(CH_2)_m CONHSO_2 R_3$,

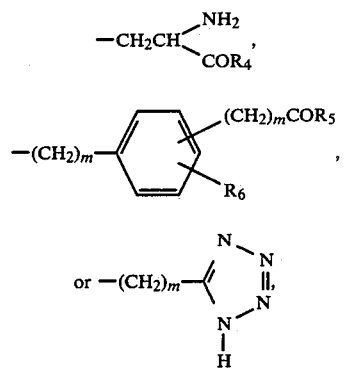

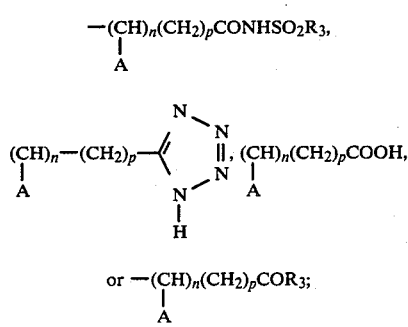

$R_3$ is alkyl, aryl, or substituted aryl;
$R_4$ is OH or Gly;
$R_5$ is OH, $C_{1-6}$alkoxy or $NHSO_2 R_3$;
$R_6$ is selected from H, $CF_3$, $C_{1-4}$alkyl, $C_{1-4}$alkoxy, F, Cl, Br, I, OH, $NO_2$, or $NH_2$; m is 0-6;
Y is

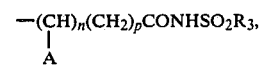

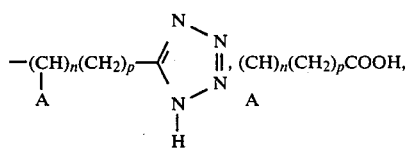

or $-(CH)_n(CH_2)_p COR_3$;
       |
       A

A is H, OH, $C_{1-4}$alkyl, $C_{1-4}$alkoxy, OAc, or F;
n is 0 or 1;
p is 0, or 1;
one of $R_1$ or $R_2$ is $C_{8-13}$alkyl, $C_{7-12}$alkoxy, phenyl $C_{4-10}$alkyl or phenyl $C_{4-10}$alkoxy and the other is H, Br, Cl, $CH_3$, $CF_3$, OH, $NO_2$ or $C_{1-4}$alkoxy;
provided that the $CONHSO_2 R_3$ moiety must be present at one or more of the R or Y positions;
or a pharmaceutically acceptable salt thereof.

This invention further relates to pharmaceutical compositions comprising a nontoxic effective amount of a compound of formula (I), or a pharmaceutically acceptable salt thereof, and a pharmaceutically acceptable carrier or diluent.

This invention also relates to pharmaceutical compositions for inhibiting antigen-induced respiratory anaphylaxis comprising a nontoxic effective amount of a compound of formula (I), or a pharmaceutically acceptable salt thereof, a histamine $H_1$-receptor antagonist, and a pharmaceutically acceptable carrier or diluent.

This invention also relates to a method of treating diseases in which leukotrienes are a factor in a subject in need thereof comprising administering to such subject a nontoxic effective amount of one of the above described compounds or pharmaceutical compositions.

DETAILED DESCRIPTION OF THE INVENTION

This invention relates to compounds represented by structural formula (I)

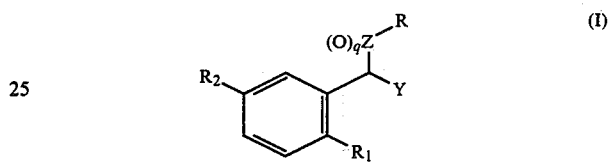

wherein:
Z is S or O;
q is 0 when Z is O and q is 0, 1 or 2 when Z is S;
R is $-(CH_2)_m CONHSO_2 R_3$, $-(CH_2)_m COOH$, $(CH_2)_m CO_2 R_3$,

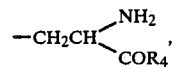

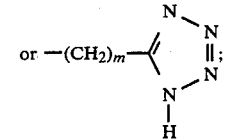

$R_3$ is alkyl, aryl, or substituted aryl;
$R_4$ is OH, or Gly;
$R_5$ is OH, $C_{1-6}$ alkoxy or $NHSO_2 R_3$;
$R_6$ is selected from H, $CF_3$, $C_{1-4}$alkyl, $C_{1-4}$alkoxy, Cl, F, Br, I, OH, $NO_2$ or $NH_2$; m is 2-6;
Y is $-(CH)_n(CH_2)_p CONHSO_2 R_3$,
   |
   A

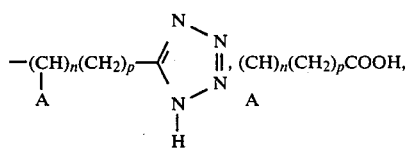

-continued or —$(CH)_n(CH_2)_pCO_2R_3$;

A

A is H, OH, $C_{1-4}$alkyl, $C_{1-4}$alkoxy, OAc, or F;
n is 0 or 1;
p is 0 or 1;
one of $R_1$ or $R_2$ is $C_{8-13}$alkyl $C_{7-12}$alkoxy, phenyl $C_{4-10}$alkyl or phenyl $C_{4-10}$alkoxy and the other is H, Br, Cl, $CH_3$, $CF_3$, OH, $NO_2$ or $C_{1-4}$alkoxy;
provided that the $CONHSO_2R_3$ moiety must be present at one or more of the R or Y positions;
or a pharmaceutically acceptable salt thereof.

A particular class of compounds of this invention are those represented by structural formula (II)

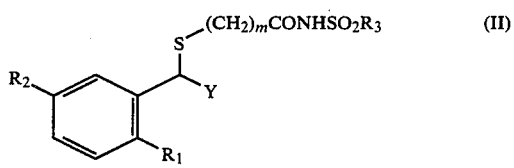

(II)

wherein $R_1$, $R_2$, $R_3$, m, and Y are as defined above in formula (I).

The compounds of formula (II) are exemplified by the following compound:
(1) 2 hydroxy 3 [2 (N phenylsulfonylcarbamoylethyl) thio]3 [2 (phenyloctyl)phenyl]propanoic acid.

A second class of compounds of this invention are those represented by structural formula (III):

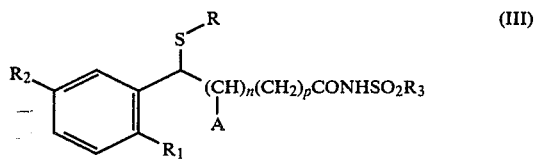

(III)

wherein A, R, $R_1$, $R_2$, $R_3$, p and n are as defined above for formula (I).

The compounds of formula (III) are exemplified by the following compounds:
(1) N [3 (carboxyethylthio)-3 [2-(8-phenyloctyl-phenyl]]propionylbenzenesulfonamide; and
(2) N [3 (carboxyethylthio) 3-[2 (8 phenyloctyl) phenyl]]propionylmethanesulfonamide.

Those compounds of the present invention which contain an acid group, are capable of forming salts with pharmaceutically acceptable bases, according to procedures well known in the art. Such bases for example include organic and inorganic bases, such as ammonia, arginine, organic amines, alkaline earth bases, alkali metal bases and transition metal bases. Of particular utility are the potassium, sodium, ammonium, magnesium, calcium, zinc, piperazine and ethylenediamine salts.

Some of the compounds of formula (I) contain one, two or more asymmetric centers. This leads to the possibility of several stereoisomers for each such compound. The present invention includes all such stereoisomers, racemates, or mixtures thereof.

To obtain compounds of formula (I) having the sulfonamide group attached at the Y position, the alkyl or arylsulfonamide is reacted with an ester compound analogous to formula (I) having a terminal ester group at the R position and a terminal acid group at the Y position, followed by optional hydrolysis of any esters present and removal of any protecting groups.

To obtain compounds of formula (I) having the sulfonamide group attached at the R position, the alkyl- or arylsulfonamide is reacted with an ester compound analogous to formula (I) having a terminal ester group at the Y position and a terminal acid group at the R position, followed by optional hydrolysis of any esters present and removal of any protecting groups.

To obtain compounds of formula (I) having sulfonamide groups attached at both the Y and R positions, the alkyl- or arylsulfonamide is reacted with a dicarboxylic acid compound having a terminal carboxylic acid group at both the R and Y positions, followed by removal of any protecting groups.

The compounds of the formula (I) wherein n and p are 0 and therefore Y is $CO_2H$, $CO_2R_3$ or $CONHSO_2R_3$ are conveniently prepared from an aldehyde precursor of the following structural formula (IV)

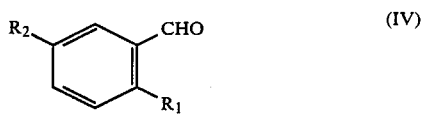

(IV)

wherein $R_1$ and $R_2$ are described above. A compound of formula (IV) is treated with trimethylsilyl cyanide in the presence of zinc iodide at low temperatures in an inert solvent to form the trimethylsilyl-protected cyanohydrin. Treatment of this with gaseous hydrogen chloride in methanol provides the methyl 2 hydroxyacetate derivative which is converted to the 2 chloroacetate with thionyl chloride. This valuable intermediate is then reacted with a mercapto acid followed by reaction in an inert solvent with an alkyl or arylsulfonamide, such as methanesulfonamide or benzenesulfonamide, in the presence of dicylohexyl-carbodiimide using an appropriate catalyst such as dimethylaminopyridine to yield a product of formula (I) after removal of any protecting groups and optional ester hydrolysis. Alternatively the 2-chloroacetate derivative may be hydrolyzed to a 2-chloroacetic acid derivative which is then reacted with a mercapto acid or a mercapto ester to give a mono- or dicarboxylic acid derivative which is then reacted with a sulfonamide as above to yield a product of formula (I) after removal of any protecting groups and optional ester hydrolysis.

The compounds of the formula (I) wherein Y is $CH_2CONHSO_2R_3$, $CH_2CO_2H$, $CH(A)CO_2H$, $CH_2CO_2R_3$, $CH(A)CO_2R_3$, or $CH(A)CONHSO_2R_3$ wherein A is H, $C_{1-4}$alkyl or $C_{1-4}$alkoxy are prepared by reacting the appropriate aldehyde of the formula (IV) and an esterified bromoacetate, conveniently t-butyl bromoacetate, with a mixture of diethyl aluminum chloride, zinc dust and a catalytic amount of cuprous bromide at low temperature in an inert solvent to give the esterified 3-hydroxypropanoate derivative which is reacted directly with a mercapto acid or mercapto ester in trifluoroacetic acid. The resulting intermediate compound is reacted with an alkyl or arylsulfonamide as described above to yield the desired product after removal of any protecting groups and optional ester hydrolysis. Alternatively, a mixture of trimethyl borate and zinc in tetrahydrofuran may be used to prepare the 3 hydroxypropanoate derivative. Alternatively an aldehyde of formula (IV) may be reacted at low temperature with the lithium salt of an esterified acetic acid, conveniently t-butylacetate or methylacetate, in an inert solvent to give the esterified 3 hydroxypropanoate derivative. By employing an esterified 2 bromopropanoate in the above reaction with an aldehyde (IV), the compounds analogous to formula (I) wherein Y is $CH(CH_3)CO_2H$ are obtained. This is reacted with a sulfonamide compound as previously described to yield a product of formula (I) after removal of any protecting groups.

To prepare the compounds Of formula (I) wherein q is 1 or 2, the appropriate thio product is conveniently oxidized with sodium periodate or meta-chloroperbenzoic acid to obtain the sulfoxide or sulfone product.

Alternatively, the compounds of the formula (I) wherein Y is $CH(A)CO_2H$, $CH(A)CO_2R_3$ or $CH(A)CONHSO_2R_3$ wherein A is H, $C_{1-4}$alkyl, $C_{1-4}$alkoxy, or fluoro are prepared from a propenoate precursor of the following structural formula (V)

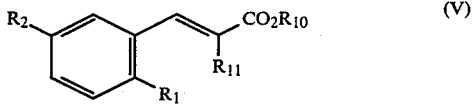

wherein $R_1$ and $R_2$ are described above, $R_{10}$ is a standard ester protective group, such as t-butyl or methyl, and $R_{11}$ is H, $C_{1-4}$alkyl, $C_{1-4}$alkoxy, or fluoro. A compound of formula (V) is reacted with a mixture of alkali metal alkoxide, such as sodium methoxide, and a mercapto acid or mercapto ester to give, after optional removal of the ester protective group, an intermediate which is reacted with a sulfonamide compound as previously described to yield a product of formula (I) after removal of any protecting groups and optional ester hydrolysis.

The propenoate precursors of formula (V) are prepared from the corresponding aldehydes of formula (IV) by general procedures such as reaction with an alkyl (triphenylphosphoranylidene)acetate or by conversion of the aldehyde- to a 3-hydroxypropionate derivative, as described above, followed by an elimination reaction to form the double bond. Additionally, the propenoate precursor is obtained from a 3-methanesulfonyloxy propionate derivative by treatment with triethylamine.

The compounds of the formula (I) wherein Y is $CH(OH)(CH_2)_pCO_2H$, $CH(OH)(CH_2)_pCO_2R_3$ or $CH(OH)(CH_2)_pCOHHSO_2R_3$ are prepared from an epoxide precursor of the following structural formula (VI)

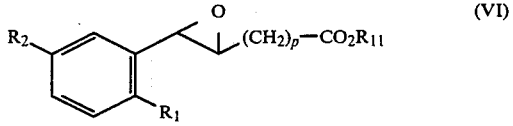

wherein $R_1$, $R_2$ and p are described above, and $R_{11}$ is lower alkyl, such as methyl or ethyl. A compound of formula (VI) is reacted in a solvent, conveniently methanol, with triethylamine and a substituted thiol selected to give, after optional removal of ester protective groups, a compound which is reacted with a sulfonamide compound as previously described to give a product of formula (I) after removal of any protecting groups and optional ester hydrolysis.

The epoxide precursors of formula (VI) where p is 0 are prepared by reaction of an aldehyde of the formula (IV) with a lower alkyl chloroacetate and an alkali metal alkoxide, such as sodium methoxide.

The compounds of formula (I) wherein Y is $CH(OH)(CH_2)_pCOOH$, $CH(OH)(CH_2)_pCONHSO_2R_3$ or $CH(OH)(CH_2)_pCO_2R_3$ can also be prepared from an ester of t following structural formula (VII)

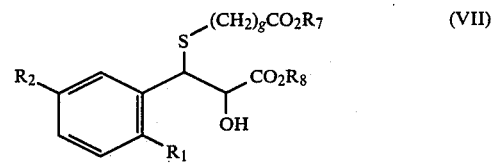

wherein $R_7$ and $R_8$ are the same or different and are $C_{1-6}$ alkyl, and g is 2. A compound of formula (VII) is reacted with sodium hydride in an inert solvent followed by reaction with a substituted benzyl bromide to yield an intermediate, which is reacted with a sulfonamide compound as previously described to give a product of formula (I) after removal of any protecting groups and optional ester hydrolysis.

The aldehydes of the formula (IV) are known or readily prepared utilizing the general procedures described as follows.

The aldehyde precursors to the compounds of the formula (I) wherein $R_1$ is, for example, an alkyl radical containing 8 to 13 carbon atoms are prepared from the appropriate 2-alkoxyphenyl-4,4-dimethyloxazoline [see Meyers et al. *J. Org. Chem.*, 43 1372 (1978)].

The aldehyde precursors of the compounds of the formula (I) wherein $R_1$ is, for example, an alkoxy radical containing 7 to 12 carbon atoms are prepared by the O-alkylation of the appropriate 2-hydroxybenzaldehyde with the corresponding alkylating agent.

The heteroaryl mercaptan precursors necessary to prepare the compounds of formula (I) are known compounds and are conveniently prepared employing standard chemical reactions. The mercapto derivatives of these precursors are prepared according to known methods. These mercaptans are reacted as described above to yield compounds of formula (I).

Appropriate modifications of the general processes disclosed, and as further described in the Examples provided hereinbelow, furnish the various compounds defined by formula (I).

Compounds of formula (I) of known chirality can be prepared by reacting a diester with a strong base to generate a thiol which is then reacted with an alkylating agent or Michael acceptor to yield an intermediate which is then reacted with a sulfonamide compound as previously described to yield a compound of formula (I) after removal of any protecting groups and optional ester hydrolysis.

An appropriate diester is represented by Formula (VIII)

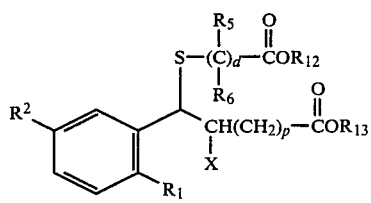

wherein
d is 2;
X is OH;
one of $R_5$ or $R_6$ adjacent to the ester group is H and the other is H or $C_{1-4}$alkyl; and $R_1$, $R_2$ and p are as defined as in formula (I) and $R_{12}$ and $R_{13}$ are independently selected from $C_{1-6}$ alkyl. Suitable strong bases include those such as sodium methoxide, sodium hydride, sodium amide, lithium diisopropyl amide or others. The reaction is conducted in an aprotic solvent such as tetrahydrofuran, dimethylsulfoxide, or N,N-dimethylformamide at ambient temperature and pressure. The resulting intermediate thiol of known chirality is represented by formula (IX)

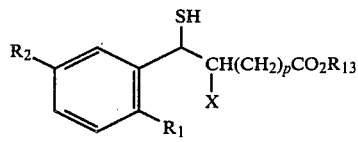

wherein $R_1$, $R_2$, $R_{13}$, X and p are as defined in formula (VIII). The thiol of formula (IX) is reacted with an alkylating agent or Michael acceptor to yield a compound which is reacted with an alkyl or arylsulfonamide as previously described to generate compounds of formula (I). Suitable alkylating agents include alkyl halides such as alkyl bromide or alkyl iodide. Benzyl halides are especially suitable to prepare compounds of formula (I). The reaction is conducted in an aprotic solvent at ambient temperature and pressure. Suitable Michael acceptors include compounds which undergo nucleophilic addition. Examples include compounds containing carbonyl, carboalkoxy, or cyano groups conjugated with a double or triple bond. Carbonyl compounds or alkynes represented by the following structural formulae are especially suitable

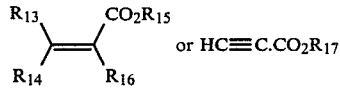

wherein $R_{13}$, $R_{14}$, and $R_{16}$ are independently selected from hydrogen or $C_{1-6}$alkyl. $R_{15}$ and $R_{17}$ are independently selected from H, aryl, or $C_{1-6}$alkyl. The reaction is conducted in an aprotic solvent at ambient temperature and pressure.

The leukotriene antagonist activity of the compounds of this invention is measured by the ability of the compounds to inhibit the leukotriene induced contraction of guinea pig tracheal tissues in vitro. The following methodology was employed:

In vitro: Guinea pig (adult male albino Hartley strain) tracheal spiral strips of approximate dimensions 2 to 3 mm cross sectional width and 3.5 cm length were bathed in modified Krebs buffer in jacketed 10 ml tissue bath and continuously aerated with 95% $O_2$/5% $CO_2$. The tissues were connected via silk suture to force displacement transducers for recording isometric tension. The tissues were equilibrated for 1 hr., pretreated for 15 minutes with meclofenamic acid (1uM) to remove intrinsic prostaglandin responses, and then pretreated for an additional 30 minutes with either the test compound or vehicle control. A cumulative concentration-response curve for $LTD_4$ on triplicate tissues was generated by successive increases in the bath concentration of the $LTD_4$. In order to minimize intertissue variability, the contractions elicited by $LTD_4$ were standardized as a percentage of the maximum response obtained to a reference agonist, carbachol (10uM).

Calculations: The averages of the triplicate $LTD_4$ concentration response curves both in the presence and absence of the test compound were plotted on log graph paper. The concentration of $LTD_4$ needed to elicit 30% of the contraction elicited by carbachol was measured and defined as the $EC_{30}$. The $-\log K_B$ value for the test compound was determined by the following equations:

$$\frac{EC_{30} \text{ (presence of test compound)}}{EC_{30} \text{ (presence of vehicle control)}} = \text{dose ratio} = X \quad 1.$$

$$K_B = \text{concentration of test compound}/(X - 1) \quad 2.$$

The compounds of this invention possess biosignificant antagonist activity against leukotrienes, primarily leukotriene $D_4$. The antagonist activity of representative compounds of this invention is listed in Table I. The $-\log K_B$ values were calculated from the above protocol. Where compounds were tested more than once, the $-\log K_B$ values given here represent the current average data.

TABLE I

Leukotriene Antagonist Activity

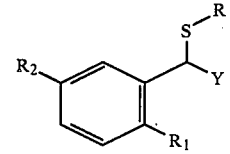

wherein $R_2$ is hydrogen, and $R_1$ is 8-phenyloctyl.

| Compound | Y | R | $-\text{Log}K_B$ |
|---|---|---|---|
| 1 | CHCOOH<br>\|<br>OH | $(CH_2)_2CONHSO_2Ph^*$ | 7.4 |
| 2 | $CH_2CONHSO_2Ph^*$ | $(CH_2)_2COOH$ | 6.5 |
| 3 | $CH_2CONHSO_2CH_3$ | $(CH_2)_2COOH$ | 6.4 |

*Ph is phenyl at each occurrence.

Pharmceutical compositions of the present invention comprise a pharmaceutical carrier or diluent and an amount of a compound of the formula (I) or a pharmaceutically acceptable salt, such as an alkali metal salt thereof, sufficient to produce the inhibition of the effects of leukotrienes, such as symptons of asthma and other hypersensitivity diseases.

When the pharmaceutical composition is employed in the form of a solution or suspension, examples of appropriate pharmaceutical carriers or diluents include: for aqueous systems, water; for non-aqueous systems, ethanol, glycerin, propylene glycol, corn oil, cottonseed oil, peanut oil, sesame oil, liquid paraffins and mixtures thereof with water; for solid systems, lactose, kaolin and mannitol; and for aerosol systems, dichlorodifluoromethane, chlorotrifluoroethane and compressed carbon dioxide. Also, in addition to the pharmaceutical carrier or diluent, the instant compositions may include other ingredients such as stabilizers, antioxidants, preservatives, lubricants, suspending agents, viscosity modifiers and the like, provided that the additional ingredients do not have a detrimental effect on the therapeutic action of the instant compositions.

The nature of the composition and the pharmaceutical carrier or diluent will, of course, depend upon the intended route of administration, i.e. parenterally, orally, topically or by inhalation.

In general, particularly for the prophylactic treatment of asthma, the compositions will be in a form suitable for administration by inhalation. Thus the compositions will comprise a suspension or solution of the active ingredient in water for administration by means of a conventional nebulizer. Alternatively the compositions will comprise a suspension or solution of the active ingredient in a conventional liquified propellant or compressed gas to be administered from a pressurized aerosol container. The compositions may also comprise the solid active ingredient diluted with a solid diluent for administration from a powder inhalation device. In the above compositions, the amount of carrier or diluent will vary but preferably will be the major proportion of a suspension or solution of the active ingredient. When the diluent is a solid it may be present in lesser, equal or greater amounts than the solid active ingredient. For aerosol/intranasal administration, a dosage of about 50 µg to 2 mg per day is suitable for adults.

For parenteral administration the pharmaceutical composition will be in the form of a sterile injectable solution or an aqueous or nonaqueous liquid suspension. A dosage of about 0.5 to 10 mg/kg is suitable for adults.

For topical administration the pharmaceutical composition will be in the form of a cream or ointment. A maximum dosage of about 500 mg per day is suitable for adults.

For oral administration the pharmaceutical composition will be in the form of a tablet, capsule or other appropriate form. A dosage of about 2 to 40 mg/kg per day is suitable for adults.

Usually a compound of formula I is administered to a human or animal subject in a composition comprising a nontoxic amount sufficient to produce an inhibition of the symptoms of an allergic response. When employed in this manner, the dosage of the composition is selected from the range of from 1 µg. to 700 mg. of active ingredient for each administration. For convenience, equal doses will be administered 1 to 4 times daily with the daily dosage regimen being selected from about 1 µg. to about 2800 mg.

The pharmaceutical preparations thus described are made following the conventional techniques of the pharmaceutical chemist as appropriate to the desired end product.

Included within the scope of this disclosure is the method of inhibiting the symptoms of an allergic response resulting from a mediator release which comprises administering to an animal subject a therapeutically effective amount for producing said inhibition of a compound of formula I, preferably in the form of a pharmaceutical composition. The administration may be carried out in dosage units at suitable intervals or in single doses as needed. Usually this method will be practiced when relief of allergic symptoms is specifically required. However, the method is also usefully carried out as continuous or prophylactic treatment. It is within the skill of the art to determine by routine experimentation the effective dosage to be administered from the dose range set forth above, taking into consideration such factors as the degree of severity of the allergic condition being treated, and so forth.

Compounds of this invention, alone and in combination with a histamine $H_1$-receptor antagonist, inhibit antigen induced contraction of isolated, sensitized guinea pig trachea (a model of respiratory anaphylaxis). Exemplary of histamine $H_1$-receptor antagonists are mepyramine, chlorpheniramine, and 2-[4-(5-bromo 3-methylpyrid-2-yl)butylamino]-5-[(6-methyl-pyrid 3-yl)methyl]-4-pyrimidone, and other known $H_1$-receptor antagonists.

Pharmaceutical compositions, as described hereinabove, of the present invention also comprise a pharmaceutical carrier or diluent and a combination of a compound of the formula (I) or a pharmaceutically acceptable salt thereof, and an histamine $H_1$-receptor antagonist in amounts sufficient to inhibit antigen-induced respiratory anaphylaxis. The above-defined dosage of a compound of formula I is conveniently employed for this purpose and the known effective dosage for the histamine $H_1$-receptor antagonist. The methods of administration described above for the single active ingredient can similarly be employed for the combination with a histamine $H_1$-receptor antagonist.

The following examples illustrate the preparation of the compounds of this invention and their incorporation into pharmaceutical compositions and as such are not to be considered as limiting the invention set forth in the claims appended hereto.

EXAMPLE 1

Preparation of
N-[3-(Carboxyethylthio)-3-[2-(8-phenyloctyl)phenyl]]-propionylbenzenesulfonamide (a) 2-(8-Phenyloctyl)benzaldehyde A solution of 8 phenyloctanoic acid (19.8 mmoles in sieve dried tetrahydrofuran (5 ml) was reduced with diborane in tetrahydrofuran (30 ml, 29.1 mmoles) at 0° C. for 4 hours to give 8-phenyloctanol. To an ice cold solution of the octanol (ca. 19.8 mmoles) and carbon tetrabromide (21.98 mmoles) in methylene chloride (50 ml) was added triphenylphosphine (22.30 mmoles) in methylene chloride (50 ml) and the resulting solution was stirred for 2.5 hours. The volatiles were evaporated and the residue was taken up in ether (100 ml), cooled in ice, and filtered. The filtrate was evaporated and distilled to afford 8-phenyloctyl bromide as an oil.

To 8-phenyloctylmagnesium bromide (from 24.25 mmoles of 8-phenyloctyl bromide and 21.27 mmoles of magnesium) in distilled tetrahydrofuran (40 ml) was added 2-(2-methoxyphenyl)-4,4-dimethyloxazoline (17.10 mmoles) [A. I. Meyers et al., *J. Org. Chem.*, 43, 1372 (1978)] in tetrahydrofuran (20 ml). After stirring for 24 hours, the reaction mixture was similarly worked up to yield 2-[2-(8-phenyloctyl)phenyl]-4,4-dimethyloxazoline as an oil. A solution of the oxazoline (11.58 mmoles) in methyl iodide (20 ml) was refluxed under argon for 18 hours. Removal of the volatiles afforded the corresponding 3,4,4-trimethyloxazolinium iodide as a white solid (mp 76.5°–78° C.). To an ice cold solution of the iodide (9.46 mmoles) in methanol (35 ml) was added in portions sodium borohydride (9.20 mmoles).

The reaction mixture was allowed to stir for 30 minutes and was then quenched with 5 percent sodium hydroxide (50 ml). The reaction mixture was extracted with diethyl ether (2×50 ml) and the extract was washed with brine (50 ml) and dried over anhydrous magnesium sulfate and filtered. Evaporation of the filtrate afforded an oil which was dissolved in acetone (50 ml), and 3N hydrochloric acid (10 ml) was added. The mixture was flushed with argon and stirred for 16 hours at ambient temperature. The volatiles were removed under vacuum and the residue partitioned between diethyl ether (50 ml) and water (50 ml). The aqueous phase was extracted with more diethyl ether (50 ml). The combined organic phase was washed with brine (50 ml) and dried over anhydrous magnesium sulfate. Evaporation of the organic phase yielded an oil which was purified by flash chromatography over silica gel with 2 percent ethyl acetate in hexane as eluant to afford the desired product as a colorless oil.

Analysis for $C_{21}H_{26}O$: Calculated: C, 85.67; H, 8.90. Found: C, 85.12, 85.22; H, 8.94, 8.96.

(b) Alternative preparation of 2-(8-phenyloctyl)-benzaldehyde

A solution of 5-hexynyl alcohol (102 mmoles) in pyridine (150 ml), under argon, was cooled to 0° C. and p-toluenesulfonyl chloride (204 mmoles) was added. The reaction mixture was kept at about 4° C. for 18 hours, poured into ice-water and then taken up in ether. The ether extract was washed with cold 10% hydrochloric acid, water and brine. The organic layer was dried and concentrated in vacuo to give 5-hexynyl p-toluenesulfonate. A solution of phenylacetylene (97 mmoles) in tetrahydrofuran (200 ml) containing a trace of triphenylmethane was cooled to 0° C. and then n-butyl lithium (37.3 ml of 2.6 moles in hexane) was added dropwise. The resulting solution was stirred at 0° C. for 10 minutes and hexamethylpho-sphoramide (21 ml) was added dropwise. After stirring for 10 minutes a solution of 5 hexynyl p-toluenesulfonate (97.1 mmoles) in tetrahydrofuran (200 ml) was added. The reaction mixture was stirred at room temperature for 18 hours, diluted with ether and the organic layer was washed with water and brine. The dried organic solution was concentrated and the product was purified by flash chromatography to qive 1 phenylocta-1,7-diyne. A mixture of this compound (43 mmoles), 2-bromobenzaldehyde (35.8 mmoles), cuprous iodide (0.5 mmoles) and bis(triphenylphosphine) palladium (II) chloride (0.7 mmoles) in triethylamine (100 ml) was heated in an oil bath (95° C.) for one hour. The reaction mixture was cooled to 0° C., filtered and the filtrate was concentrated. The residue was dissolved in ether, washed with 10% hydrochloric acid, water and brine. The organic layer was dried and concentrated to give a product which was purified by flash chromatography to yield 2-(8-phenyl-1,7-octadiynyl)benzaldehyde. A solution of this compound (24 1 mmoles) in ethyl acetate (100 ml) and 10% palladium on charcoal (1 g) was hydrogenated (40 psi of hydroqen) at room temperature for 15 minutes. The catalyst was filtered off and the filtrate concentrated to give the 2-(8-phenyloctyl)benzaldehyde.

(c) t-Butyl 3-hydroxy-3-[2-(8-phenyloctyl)phenyl]propanoate

A solution of diisopropylamine (4.8 ml, 0.03 mole) in tetrahydrofuran/hexane (100 ml, 1/1) was cooled to 60° C. and n-butyllithium (2.5M solution in hexane, 13.6 ml, 0.03 mole) was added. This solution was stirred for 10 minutes followed by addition of t-butyl acetate (4.6 ml, 0.03 mole). The mixture was stirred for an additional 10 minutes followed by dropwise addition of a solution of 2-(8-phenyloctyl)benzaldehyde (10 gm, 0.03 mole) in tetrahydrofuran (25 ml). The whole was stirred first for 30 minutes at −50° C. and then for 30 minutes at 20° C. The reaction mixture was poured into aqueous acid and extracted twice with diethyl ether. The combined extracts were washed with 5% aqueous sodium bicarbonate solution and saturated aqueous sodium chloride solution and then dried over anhydrous magnesium sulfate, filtered and evaporated. Chromatography on silica gel using hexane-ethyl acetate (95/5) to elute gave the product as an oil. 90 MHz NMR (CDCl$_3$) δ 1.29–1.52 (12H,m) 2.52–2.78 (6H,m) 5.39 (1H,dd) 7.10–7.60 (9H,m).

(d) 3-[(2-carbomethoxyethyl)thio]-3-[2-(8-phenyloctyl)-phenyl]propanoic acid

A solution of t-butyl 3-hydroxy-3-[2-(8-phenyloctyl)-phenyl]propanoate (4.0 gm, 9.7 mmole) in methylene chloride (40 ml) was stirred under an inert atmosphere at −10° C. To this cold solution was added methyl 3-mercaptopropionate (6.2 ml, 56 mmole) in one portion followed by dropwise addition of trifluoroacetic acid (80 ml). The reaction mixture was then stirred for 5 hours at 0° C. Solvent and excess trifluoroacetic acid were removed on a rotary evaporator. The residue was redissolved in methylene chloride and washed twice with water and once with saturated aqueous sodium chloride solution, dried over anhydrous magnesium sulfate, filtered and evaporated. Chromatography on silica gel eluting with hexane-ethyl acetate formic acid (85/15/0.5) gave the title compound. Anal.: Calcd. for $C_{27}H_{36}O_4S$: C, 71.17; H, 7.74. Found: C, 70.46; H, 7.72. 250 MHz NMR (CDCl$_3$) δ 1.28–1.68 (12H,m) 2.48 (2H,t) 2.56–2.72 (6H,m) 2.93 (2H,d) 3.66 (3H,s) 4.60 (1H,t) 7.18–7.39 (9H,m).

(e) N-[3 -(carboxyethylthio)-3-[2 (8-phenyloctyl)phenyl]]propionylbenzenesulfonamide 3 -[(2-Carbomethoxyethyl)thio]-3 -[2 -(8 phenyloctyl)phenyl]propanoic acid (1 gm) was dissolved in methylene chloride (10 ml) and benzenesulfonamide (0.38 gm), dicyclohexylcarbodiimide (0.454 gm) and a catalytic amount of 4 dimethylaminopyridine (27 mg) were added. The mixture was stirred at room temperature for 18 hours. The solids were filtered off and the filtrate was evaporated. The residue was taken up in diethyl ether and the above filtration repeated. The final residue, after removal of the ether, was dissolved in acetonitrile (18 ml) and 1N hydrochloric acid (6 ml) was added. This mixture was refluxed for 24 hours. The resulting solution was evaporated, and the residue was partitioned between methylene chloride and water. The organic phase was washed with water and saturated sodium chloride solution and then dried over anhydrous magnesium sulfate, filtered and evaporated. The product was obtained after chromatography on silica gel. 250 MHz NMR (CDCl$_3$)δ 1.2–1.68 (12H, m) 2.42–2.98 (10H, m) 4.62 (1H, dd) 7.05–7.51 (13H, m) 7.89 (1H, d). Mass spectrum (DCl/NH$_3$) m/z 599 (M+NH$_4$)+ IR(cm$^{-1}$) 1715 (C=O of COOH) 1345, 1180 (SO$_2$NH).

EXAMPLE 2

Preparation of N-[3-(carboxyethylthio)-3-[2 (8 phenyloctyl)phenyl]propionyl]methanesulfonamide 3-[(2 Carbomethoxyethyl)thio]-3-[2-(8 phenyloctyl) phenyl]propanoic acid (1 gm) prepared as in Example 1(d) was dissolved in methylene chloride (10 ml) and methanesulfonamide (0.23 gm), dicyclohexylcarbodiimide (0.454 gm) and a catalytic amount of 4-dimethylaminopyridine (27 mg) were added. The mixture was stirred at room temperature for 18 hours. The solids were filtered off and the filtrate was evaporated. The residue was chromatographed on silica gel to give N-[(3-carbomethoxyethyl)thio]-3-[2-(8-phenyloctyl)-phenyl]propionylmethane sulfonamide, which was dissolved in methanol (7.5 ml). To this solution was added 1N hydrochloric acid (2.5 ml) and the mixture was refluxed for 20 hours, cooled to room temperature and extracted with methylene chloride three times. The combined extracts were washed with water and saturated sodium chloride solution, dried over anhydrous magnesium sulfate, filtered and evaporated. The product mixture was purified by preparative layer chromatography to give the title compound. 90 MHz NMR (CDCl$_3$) δ 1.05–1.80 (12H, m) 2.3–3.0 (10H, m) 3.1 (3H, s) 4.62 (1H, t) 7.0–7.48 (9H, bs) 9.46 (2H, bs). Mass spectrum (DCI/NH$_3$) m/z 520 (M+H)$^+$ 518 (M−H)$^+$ IR(CM$^{-1}$) 1710 (C=O of COOH) 1345, 1170 (SO$_2$NH).

EXAMPLE 3

Preparation of 2-Hydroxy-3-[2-(N-phenylsulfonylcarbamoylethyl)thio]-3-[2-(8 phenyloctyl)phenyl]propanoic acid

(a) Methyl 3-[2-(8 phenyloctyl)phenyl]2,3-epoxypropanoate

The compound of Example 1(a) (2.94 g, 10 mmoles) was dissolved in diethyl ether (25 ml) and the solution was stirred under argon at 0° C. Methyl chloroacetate (1.32 ml, 15 mmoles) was added, followed by the addition of sodium methoxide (810 mg, 15 mmoles). The mixture was stirred for 2.5 hours at ice bath temperature. A small quantity of water was added, the ether phase separated, dried over anhydrous sodium sulfate, filtered and evaporated. The residue was flash chromatographed on 80 grams of silica gel eluted with 5–30% ethyl acetate/hexane to give the product.

(b) Methyl 3-(2-carbomethoxyethylthio)-3-[2-(8-phenyloctyl)phenyl]-2-hydroxypropanoate The compound of Example 3(a) (1.2 g, 3.28 mmoles) was dissolved in methanol (20 ml) containing 2% triethylamine and stirred under argon at room temperature. Methyl 3-mercaptopropionate (0.623 ml, 5.45 mmoles) and triethylamine (1.45 ml, 9.84 mmoles) were dissolved in methanol (15 ml) and added dropwise. The mixture was stirred for 18 hours. The solvent was stripped and the residue was flash chromatographed on silica gel eluted with 20% ethyl acetate/hexane to give a mixture of the desired product and its regioisomer, methyl 2-(2-carbomethoxyethylthio)-3-[2-(8 phenyloctyl)phenyl]-3-hydroxypropanoate. The mixture was rechromatographed on 100 grams of neutral alumina to separate the desired product.

(c) Methyl 2-t-butyldiphenylsilyloxy-3-[(2-carbomethoxyethyl)thio]-3-[2-(8-phenyloctyl)phenyl]propanoate The compound of Example 3(b) above (10.3 gm, 0.021 mole) was dissolved in dry N,N-dimethylformamide (50 ml). To this solution was added t-butyldiphenyl silylchloride (6.1 ml, 0.023 mole) and imidazole (3.2 gm, 0.047 mole), and the whole was stirred at 40° C. for 5 hours. The reaction was then diluted to 250 ml with water and extracted three times with diethyl ether. The combined ether extracts were washed three times with water and once with saturated sodium chloride solution, dried over anhydrous magnesium sulfate, filtered and evaporated to give the product as an oil. 90 MHz NMR (CDCl$_3$) 0.80 (9H, s) 1.22–1.78 (12H, m) 2.21–2.82 (8H, m) 3.26 (3H, s) 4.30 (1H, d) 4.50 (1H, d) 7.01–7.78 (19H, m).

(d) Methyl 2-t butyldiphenylsilyloxy-3-[(2-carboxyethyl)thio]-3-[2(-8-phenyloctyl)phenyl]propanoate The compound of example 3(c) (15.3 gm, 0.021 mole) was dissolved with stirring in methanol (300 ml) under argon at room temperature. The solution was then cooled in an ice bath while 60 ml of 1M sodium hydroxide solution was added dropwise with rapid stirring over a 15 minute period keeping the temperature of the reaction mixture below 23° C. The resulting solution was stirred at room temperature for 6 hours. Methanol was then removed by evaporation, and the residue was diluted with water (150 ml) and adjusted to pH 4–5 with 1N HCl. The aqueous solution was extracted into ethyl acetate (100 ml) three times and the combined organic phases were washed with saturated aqueous sodium chloride solution, dried over anhydrous magnesium sulfate, filtered and evaporated. The product was chromatographed on silica gel to give the title compound as an oil. 90 MHz NMR (CDCl$_3$)δ 0.82 (9H, s) 1.2–1.7 (12H, m) 2.24–2.82 (8H, m) 3.23 (3H, s) 4.30 (1H, d) 4.50 (1H, d) 7.08–7.60 (19H, m). IR(cm$^{-1}$) 3485 (OH of COOH) 1745 (C=O of COOME) 1715 (C=O of COOH).

(e) 2-Hydroxy-3-[2-(N-phenylsulfonylcarbamoyl ethyl)thio]-3-[2-(8-phenyloctyl)phenyl]-propanoic acid The compound in Example 3(d) above (1 gm) was dissolved in methylene chloride (10 ml) and benzene sulfonamide (0.24 gm, 1.54 mmole), dicyclohexyl carbodiimide (0.29 gm, 1.4 mmole) and 4-dimethyl aminopyridine (17 mg, 0.14 mmole) were added. The mixture was stirred at room temperature overnight. Solids were filtered off and washed with methylene chloride, and the filtrate evaporated. The residue was chromatographed on silica gel to give methyl 2-t-butyldiphenylsilyloxy-3-[2-(N-phenylsulfonylcarbamoylethyl)thio]-3-[2-(8-phenyloctyl)phenyl]propanoate. Cleavage of the silyl ether by standard treatment with tetra-n-butylammonium fluoride followed by hydrolysis of the methyl ester with sodium hydroxide in methanol/tetrahydrofuran as described in Example 3(b) above gave the title compound after final silica gel chromatography. 250 MHz NMR (CDCl$_3$) δ 1.2–2.8 (20H, m) 4.58 (1H, d) 4.69 (1H, d) 7.10–7.60 (8H, m) 8.06 (1H, d). Mass spectrum (DCI/NH$_3$) m/z 615 (M+NH$_4$)$^+$.

EXAMPLE 4

Preparation of 2-[3-(N-phenylsulfonylcarbamoylpropyl)thio]-2-(2-dodecylphenyl)acetic acid

(a) 2-(2-Dodecylphenyl)-4,4-dimethyloxazoline

To freshly prepared dodecylmagnesium bromide (from 30.13 mmoles of dodecyl bromide and 26.20 mmoles of magnesium) in distilled tetrahydrofuran (50 ml) was added 2-(2-methoxyphenyl) 4,4-dimethyloxazoline [A. I. Meyers et al., *J. Org. Chem.*, 43, 1372 (1978)] (17.88 mmoles) in tetrahydrofuran (30 ml). The resultant yellow solution was stirred under argon at ambient temperature for 20 hours. The solution was cooled in an ice water bath and quenched with aqueous ammonium chloride (100 ml). The reaction product was extracted into diethyl ether (100 ml) and the organic phase was washed with saturated sodium chloride solution (50 ml) and then dried over anhydrous magnesium sulfate. Evaporation of the organic phase afforded a colorless oil which was purified by flash chromatography over silica gel with 5 percent ethyl acetate in hexane as eluant to afford the desired product as a pale yellow oil.

Analysis for $C_{23}H_{37}NO$: Calculated: C, 80.41; H, 10.85; N, 4.08. Found: C, 80.22; H, 10.56; N, 3.87.

(b) 2-(2-Dodecylphenyl)-3,4,4-trimethyloxazolinium iodide

A solution of the compound of Example 4(a) (17.2 mmoles) in methyl iodide (20 ml) was refluxed under argon for 18 hours. The volatiles were removed under vacuum and the solid residue triturated with ethyl acetate (25 ml) to afford the desired product as white crystals (mp 78°–84° C.).

(c) 2-Dodecylbenzaldehyde

To an ice cold solution of the compound of Example 4(b) (10.0 mmoles) in methanol (50 ml) over a period of 15 minutes was added in small portions sodium borohydride (10.0 mmoles). The reaction mixture was allowed to stir for 30 minutes and was then quenched with 5 percent sodium hydroxide (50 ml). The reaction mixture was extracted with diethyl ether (2×50 ml) and the extract was washed with brine (50 ml) and dried over anhydrous magnesium sulfate. Evaporation of the extract afforded an oil which was dissolved in acetone (50 ml) and 3N hydrochloric acid (10 ml) was added. The mixture was flushed with argon and stirred for 16 hours at ambient temperature. The volatiles were removed under vacuum and the residue partitioned between diethyl ether (50 ml) and water (50 ml). The aqueous phase was extracted with more diethyl ether (50 ml). The combined organic phase was washed with brine (50 ml) and dried over anhydrous magnesium sulfate. Evaporation of the organic phase yielded an oil which was purified by flash chromatography over silica gel with 2 percent ethyl acetate in hexane as eluant to afford the desired product as a colorless oil.

Analysis for $C_{19}H_{30}O$: Calculated: C, 83.15; H, 11.02. Found C, 82.59; H, 10.65.

(d) Methyl 2-(2-dodecylphenyl)-2-hydroxy acetate

The compound of Example 4(c) (17.2 mmoles) was dissolved in methylene chloride (20 ml) and stirred at 0° C. under argon. Zinc iodide (1.87 mmoles) was added, followed by the dropwise addition of trimethylsilyl cyanide (2.45 ml, 18.3 mmoles) dissolved in methylene chloride (30 ml). After 1 hour at 0° C. the ice bath was removed and the mixture stirred for 1 hour at room temperature. The solvent was stripped and methanol (100 ml) was added after the residue was cooled in an ice bath. Excess hydrogen chloride was bubbled into the solution while the mixture was stirred at ice bath temperature. The ice bath was then removed and the mixture stirred at room temperature for 18 hours. Water (20 ml) was added and the mixture stirred for 2 hours. The solvent was evaporated and the aqueous residue extracted with ethyl acetate. The combined organic phases were dried over anhydrous sodium sulfate, filtered and evaporated. The crude product was flash chromatographed on silica gel, eluted with 20% ethyl acetate/hexane, to give the product as a clear colorless liquid.

(e) Methyl 2-Chloro-2-(2-dodecylphenyl)acetate

The compound of Example 4(d) (12 mmoles) was stirred under argon in an ice bath and thionyl chloride (20 ml) was added in a single portion. The ice bath was removed and the mixture was stirred under argon for 18 hours. The solvent was stripped and the residue flash chromatographed on 200 grams of silica gel eluted with 20% methylene chloride/carbon tetrachloride to give the product as a clear colorless liquid.

(f) Methyl 2-(3-carboxypropylthio)-2-(2-dodecylphenyl)acetate

The compound of Example 4(e) (1 mmole), 4-mercaptobutyric acid (1.33 mmoles), and triethylamine (3 mmoles) were dissolved in methylene chloride (25 ml) and stirred at room temperature under argon for 5 days. The solvents were pumped off and the residue flash chromatoqraphed on 50 grams of silica gel eluted with 6:3:1 methylene chloride:ethanol:ammonium hydroxide. The eluant was concentrated, acidified with hydrochloric acid, extracted with ethyl acetate, dried over anhydrous sodium sultate, filtered and evaporated to give the product. $^1H$ NMR (90 MHZ, $CDCl_3$)δ 0.9(t,3H), 1.1–2.8(m,28H), 3.6(s,3H), 4.8(s,1H), 7–7.2(m,3H), 7.4–7.5 (m,1H).

(g) 2-(3-(N-phenylsulfonylcarbanoylpropyl)thio]-2-(2-dodecylphenyl)acetic acid The compound of example 4(f) is treated according to the process in example 1(e) to yield the desired titled compound.

EXAMPLE 5

Preparation of 3-[2--(N-phenylsulfonylcarbamoylethyl)thio]-3-(2-dodecylphenyl)propanoic acid

(a) Methyl 3-(2-dodecylphenyl)propenoate

The compound of Example 4(c) (32 mmoles) was dissolved in toluene (50 ml) and cooled to 0° C. in an ice-water bath while stirring under argon. Methyl (triphenylphosphoranylidene)acetate (32 mmoles) was added in one portion. The mixture was heated at 110° C. for 24 hours. The toluene was evaporated and the resulting residue was flash chromatographedusing a 6% ethyl acetate in hexane system to give the product.

(b) Methyl 3-(2-carboxyethylthio)-3-(2-dodecylphenyl)propanoate

Sodium (155.5 mmoles) was added slowly to methanol (200 ml) under an atmosphere of argon. The mixture was cooled to 0° C. in an ice bath and 3-mercaptopropanoic acid (78 mmoles) was added dropwise. This mixture was stirred for 30 minutes and the compound of Example 5(a) (7.8 mmoles) was added dropwise. The reaction mixture was stirred for 24 hours. The solvent was evaporated. The residue was taken up in ice water and acidified with 10% phosphoric acid to a pH of 6.5. The product was extracted into ethyl acetate. The combined organic extracts were dried over magnesium sulfate, filtered and evaporated. The resulting residue was flash chromatographed with 1.0% methanol and 1.0% formic acid in methylene chloride. This provided the product as an oil.

(c) 3-[2-(N-phenylsulfonylcarbamoylethyl)thio]-3-(2-dodecylphenyl)propanoic acid The compound of example 5(b) is treated according to the process of example 1(e) to yield the desired titled product.

EXAMPLE 6

Preparation of 2-Methyl-3-[2-(N-phenylsulfonylcarbamoylethyl)thio]-3-(2-dodecylphenyl)propanoic acid (a) Methyl 2-methyl 3-hydroxy-3-(2-dodecylphenyl) propanoate To a suspension of zinc dust (15 mmoles) and copper (I) bromide (5 mmoles) in distilled tetrahydrofuran (10 ml) at 25° C. was added diethylaluminum chloride (10 mmoles). The mixture was stirred for 5 minutes, then cooled to 0° C. in an ice methanol bath. A solution of the compound of Example 1(c) (10 mmoles) and methyl d,1-2-bromopropionate (10 mmoles) in tetrahydrofuran (10 ml) was added dropwise to the cold suspension. The resulting mixture was stirred for 3 hours at 25° C. The reaction mixture was filtered and the filtrate was washed with water, dried over magnesium sulfate, and evaporated to give the product.

(b) Methyl 2-methyl-3-(2-carboxyehylthio)-3-(2-dodecylphenyl)-propanoate

To a solution of trifluoroacetic acid (15 ml) and 3-mercaptopropanoic acid (2.4 ml) at 0° C. was added the compound of Example 6(a). The reaction mixture was stirred for 3 hours and evaporated. The resulting residue was flash chromatographed on silica, eluted with 20% ethyl acetate in hexane, to give a mixture of erythro and threo isomers of the product. $^1$H NMR (CDCl$_3$) δ: 0.9 (t, J=6.5 Hz,3H), 1.35(m,23H), 2.5(m,6H), 3.0(t, J=6.5,1H), 3.5(s,3H), 4.5(d,J=6.5,1H), 7.2(m,3H), 7.5(m,1H), 10(bs,1H). $^1$H NMR (CDCl$_3$) 67 : 0.9(t,J=6 Hz,3H), 1.3(m,23H), 2.5(m,6H), 3.0(dd, J=6 Hz, 11 Hg, 1H), 3.75(s,3H), 4.3(d, J=11 Hz,1H), 7.2(m,4H), 9.2(bs,1H).

(c) 3-[(2-N-phenylsulfonylcarbamoylethyl)thio]-3-(2-dodecylphenyl)propanoic acid The compound of Example 6(b) is treated according to the process of Example 1(e) to yield the desired titled product.

EXAMPLE 7

Preparation 3-[2-(N-phenylsulfonylcarbamoylethyl)thio]-3-[2-(8 phenyloctyl)-5-trifluoromethvlphenyl]propanoic acid (a) 2-(8-Phenyloctyl)-5-trifluoromethyl benzaldehyde To a solution of 2-bromo-5-trifluoromethyl benzonitrile (20.16 mmoles) in methylene chloride (50 ml), under argon at room temperature, was added diisobutylaluminum hydride (25 mmoles, 25 ml hexane) dropwise and the resulting solution was stirred for 30 minutes. The reaction mixture was diluted with ether (50 ml), cooled in ice and quenched by the careful addition of hydrochloric acid (50 ml, 3N). The ice bath was removed and the mixture was stirred vigorously for 15 minutes. The organic layer was washed with brine (50 ml), treated with magnesium sulfate charcoal and evaporated. The resulting oil was purified by distillation to give 2 bromo 5-trifluoromethyl benzaldehyde, bp 50°-55° C. at 0.05 mm Hg. A mixture of this compound (16.24 mmoles), 1 phenylocta-1,7-diyne (19.54 mmoles, prepared as in Example 1b), cuprous iodide (0.19 mmole) and bis(triphenylphosphine) palladium (II) chloride (0.34 mmole) in triethylamine (50 ml) was refluxed under argon for 30 minutes. The reaction mixture was cooled and filtered. The filtrate was evaporated, taken up in ether (100 ml), washed with hydrochloric acid (50 ml, 3N) and sodium chloride, and treated with magnesium sulfate charcoal. Filtration and evaporation left an oil which was purified by flash chromatography (5% ether/hexane) to yield 2-(8-phenyloctadiyn-1,7-yl)-5-trifluoromethyl benzaldehyde as an oil. A solution of this compound (13.26 mmoles) in ethyl acetate (100 ml) was treated with charcoal for 30 minutes and then filtered. The solution was then shaken under 50 psi of hydrogen with 10% palladium on charcoal (502 mg) for about 90 minutes. Thin layer chromatography of the reaction mixture indicated about 50% reduction of the aldehyde to the alcohol. To re-oxidize the alcohol, the palladium catalyst was filtered off and manganese dioxide (20 g) was added. This mixture was then stirred at room temperature under argon for 18 hours. Filtration and evaporation gave an oil which was purified by flash chromatography (2% ether/hexane) to afford the product as an oil.

(b) Methyl 3-[2-(8-phenyloctyl)-5-trifluoro methylphenyl]-3-hydroxypropanoate

The compound of Example 7(a) (5.1 mmoles) in tetrahydrofuran (7 ml) and trimethyl borate (7 ml) were added dropwise with stirring to zinc metal (8.8 mmoles) at 25° C. After 5 minutes, methyl bromoacetate (6.79 mmoles) was added all at once and the mixture was stirred for 24 hours. An additional 2 ml. of methyl bromoacetate was added and the mixture stirred at room temperature for 36 hours The reaction mixture was diluted with ether, cooled to 0° C., and ice cold ammonium hydroxide/water/glycerine was added dropwise with stirring. The organic layer was washed with water and brine, dried over magnesium sulfate and concentrated. The residue was flash chromatoqraphed on silica, eluted with 5% ethyl acetate/hexane, to give the product as a clear colorless oil.

(c) Methyl 3-[2-(8-phenyloctyl)-5-trifluoromethylphenyl]-3-methanesulfonyloxypropanoate The compound of Example 7(b) (2.0 mmoles) was dissolved in methylene chloride (10 ml) under argon and the solution cooled to −10° C. Triethylamine (6.6 mmoles) was added and then methanesulfonyl chloride (2.2 mmoles) in methylene chloride (3 ml) was added dropwise. The mixture was stirred in the cold for 30 minutes and poured into ice/water/methylene chloride. The separated organic layer was washed with cold ammonium chloride solution, water and brine, and then dried and concentrated to give the product as an oil.

(d) Methyl 3-[2-(8-phenyloctyl)-5-trifluoromethylphenyl]propenoate

The compound of Example 7(c) (1.97 mmoles) was dissolved in methylene chloride (10 ml) under argon and the solution cooled to 0° C. Triethylamine (6.3 mmoles) in methylene chloride (5 ml) was added dropwise and the mixture allowed to warm to room temperature for 18 hours and poured into ice/water/methylene chloride. The separated organic layer was washed with cold ammonium chloride solution, water and brine, and then dried and concentrated to qive the product as an oil.

Alternatively, the compound of Example 7(a) is reacted with methyl (triphenylphosphoranylidene)acetate to give the product of Example 7(d).

(e) Methyl 3-(2-carboxyethylthio)-[2-(8-phenyloctyl)-5-trifluoromethylphenyl]propanoate Following the procedure of Example 5(b) the compound of Example 7(d) (1.86 mmoles) was converted to the titled product.

(f) 3-[2-(N-phenylsulfonylcarbamoylethyl)thio]-3-[-2-(8-phenyloctyl)-5-trifluoromethylphenyl]propanoic acid The compound of Example 7(e) is treated according to the process of Example 1(e) to yield the desired titled compound.

EXAMPLE 8

Preparation of 2-Hydroxy-3-[2-(N-methylsulfonylcarbamoylethyl)thio]-3-[2-(8-phenyloctylphenyl)]-propanoic acid

(a) Methyl 3-[2-(8-phenyloctyl)phenyl]-2,3-epoxypropanoate

The compound of Example 1(a) (2.94 q, 10 mmoles) was dissolved in diethyl ether (25 ml) and the solution was stirred under argon at 0° C. Methyl chloroacetate (1.32 ml, 15 mmoles) was added, followed by the addition of sodium methoxide (810 mg, 15 mmoles). The mixture was stirred for 2.5 hours at ice bath temperature. A small quantity of water was added, the ether phase separated, dried over anhydrous sodium sulfate, filtered and evaporated. The residue was flash chromatographed on 80 grams of silica gel eluted with 5–30% ethyl acetate/hexane to give the product.

(b) Methyl 3-(2-carbomethoxyethylthio)-3-[2-(8-phenyloctyl)-phenyl]-2-hydroxypropanoate The compound of Example 8(a) (1.2 q, 3.28 mmoles) was dissolved in methanol (20 ml) containing 2% triethylamine and stirred under argon at room temperature. Methyl 3-mercaptopropionate (0.623 ml, 5.45 mmoles) and triethylamine (1.45 ml, 9.84 mmoles) were dissolved in methanol (15 ml) and added dropwise. The mixture was stirred for 18 hours. The solvent was stripped and the residue eluted with 20% ethyl acetate/hexane to qive a mixture of the desired product and its regioisomer, methyl 2-(2-carbomethoxyethylthio)-3-[2-(8-phenyloctyl)phenyl]-3-hydroxypropionate. The mixture was rechromatographed on 100 grams of neutral alumina to separate the desired product.

(c) 3-(2-carboxyethylthio)-3-[2-(8-phenyloctyl)phenyl]-2-hydroxypropanoic acid The desired product of Example 8(b) (320 mg, 0.66 mmole) was dissolved in methanol (10 ml) and stirred under argon at ice bath temperature. A 1N solution of sodium hydroxide (2.5 ml, 2.5 mmoles) was added dropwise, the ice bath removed, the mixture stirred at room temperature for 2.5 hours, and then cooled for 18 hours. After an additional 1 hour of stirring at room temperature, the methanol was stripped, the residue diluted with water and the pH adjusted to 3.5 with dilute hydrochloric acid. Extraction with ethyl acetate followed by drying over anhydrous sodium sulfate, filtration and evaporation gave the crude product which was flash chromatoqraphed on 20 grams of silica gel eluted with 30:70:0.5 ethyl acetate:hexane:formic acid to qive the free acid product.

(d) 2-Hydroxy-3-[(2-carboisopropoxyethyl)thio]-3-[2-(8-phenyloctylphenyl)]propanoic acid A solution of 1 gm of 2-hydroxy- 3-[(2-carboxyethyl)-thio]-3-[2-(8-phenyloctyl)phenyl]propanoic acid in 10 ml isopropanol was treated with qaseous hydrogen chloride for 5 minutes. The resultinq solution was stirred for an additional 5 minutes; the solvent was removed on a rotary evaporator; and the residue was taken up in methylene chloride. This solution was washed successively with water and saturated aqueous sodium chloride solution, dried over anhydrous maqnesium sulfate, filtered and evaporated. Chromatography on silica gel using hexane-ethyl acetate formic acid (65/35/0.5) gave the title compound.

ANAL:Calcd for $C_{29}H_{40}O_5S$: C, 69.87; H, 8.08; S, 6.40. Found: C, 68.76; H, 7.79; S, 6.42. 250 MHz NMR (CDCl$_3$) δ1.22 (6H,d) 1.28–1.68 (12H,m) 2.50–2.90 (8H,m) 4.62 (1H,d) 4.72 (1H,d) 5.06 (1H, septet) 7.10–7.62 (9H,m).

(e) 2-Hydroxy-3-[2-(N-methylsulfonylcarbamoylethyl)thio]-3-[2-(8-phenyloctylphenyl)]propanoic acid The compound of Example 8(d) is reacted according to the process of Example 3 using methanesulfonamide to yield the desired titled product.

EXAMPLE 9

Preparation of 2-Hydroxy-3-[4-(N methylsulfonylcarbamoylphenyl)thio]-3-[2-(8-phenyloctyl)phenyl]propionylmethanesulfonamide

(a) Methyl 2-hydroxy-3-(4-carbomethoxyphenylthio)-3-[2-(8-phenyloctyl)phenyl]propanoate A mixture of the compound of Example 3(a) (644 mq, 1.76 mmol), and p mercaptobenzoic acid (325 mq, 2.11 mmol), prepared according to Wiley, P. F., *J. Org. Chem.*, 16, 812 (1951) herein incorporated by reference, in 10 ml of methanol and 0.6 ml of triethylamine was stirred at 23° for 16 hours. The solution was treated with 1 ml of 25% NaOMe in methanol, stirred 3 hours, poured into 0.5N hydrochloric acid and extracted with ethyl acetate. The extracts were dried and the solvent evaporated. The residue was esterified with methanol and qaseous HCl, and then chromatographed over silica gel. The product was eluted with a mixture of ethyl acetate and hexane (30:70), and gave 350 mg (37%). nmr $CDCl_3$:4.90(d,1H), 4.50(5,1H).

(b) 2-Hydroxy-3-(4-carboxyphenylthio)-3-[2-(8-phenyloctyl)phenyl]propanoic acid.

The compound of Example 9(a) (0.28 mmol) in 5 ml methanol was treated with 2 ml of 0.5N NaOH, and stirred at 23° for 2 hours. The reaction was diluted with 10 ml of water, filtered, the filtrate acidified, and extracted with ethyl acetate. The extracts were dried and evaporated and gave the titled product in 48% yield after recrystallization from a mixture of benzene and hexane. nmr($CDCl_3$/$Me_2CO$):8.00(d,2H), 7.00–7.88(m,14H), 5.12(d, J=4.3 Hz,1H), 4.67(d,J=4.3 Hz,1H), 2.40–2.90(m,4H), 1.10–1.76 (m,12H).

(c) 2-Hydroxy-3-[4-(N-methylsulfonylcarbamoylphenylthio)-3-[2-(8-phenyloctyl)phenyl]propionylmethanesulfonamide The compound of Example 9(b) was treated according to Example 2 through the chromatography on silica gel to yield the desired titled product.

EXAMPLE 10

As a specific embodiment of a composition of this invention, 1 to 10 mg/ml of an active ingredient, such as the compound of Example 3 is dissolved in isotonic saline solution and aerosolized from a nebulizer operating at an air flow adjusted to deliver the desired aerosolized weight of drug.

EXAMPLE 11

As an additional embodiment of a composition of this invention, 100 mg of an active ingredient, such as the compound of Example 1 or 2 is combined with 4 mg of chlorophenirmine maleate with a suitable carrier or excipient.

What is claimed:

1. A compound represented by the following structural formula (I):

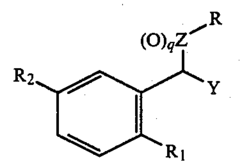

(I)

wherein:

Z is S or O;

q is 0 when Z is O and q is 0, or 2 when Z is S;

R is $-(CH_2)m$ $CONHSO_2R_3$, $-(CH_2)_mCOOH$, $(CH_2)_mCO_2R_3$, 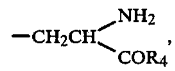 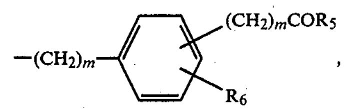 or $R_3$ is alkyl, or aryl;

$R_4$ is OH, or Gly;

$R_5$ is OH, $C_{1-6}$ alkoxy, or $NHSO_2R_3$;

$R_6$ is selected from H, $CF_3$, $C_{1-4}$ alkyl, $C_{1-4}$ alkoxy, F, Cl, Br, I, OH, $NO_2$, or $NH_2$;

m is 0–6;

Y is

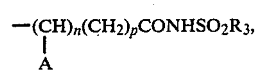

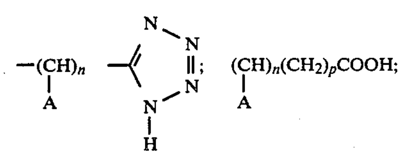

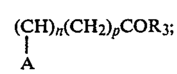

A is H, OH, $C_{1-4}$alkyl, $C_{1-4}$alkoxy, OAc, or F;

n is 0 or 1; p is 0 or 1;

one of $R_1$ or $R_2$ is $C_{8-13}$alkyl, $C_{7-12}$alkoxy, phenyl $C_{4-10}$alkyl or phenyl $C_{4-10}$alkoxy and the other is H, Br, Cl, $CH_3$, $CF_3$, OH, $NO_2$ or $C_{1-4}$ alkoxy;

provided that the $CONHSO_2R_3$ moiety must be present at one or more of the R or Y positions; or a pharmaceutically acceptable salt thereof.

2. A compound of claim 1 represented by the following structural formula (II):

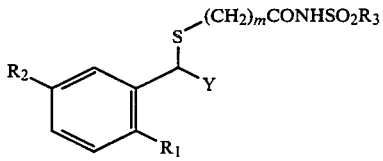

3. A compound of claim 2 which is 2-hydroxy-3-[2-(N-phenylsulfonylcarbamoylethyl)thio]-3-[2-(8-phenyloctyl)phenyl]propanoic acid.

4. A compound of claim 1 represented by the following structural formula (III):

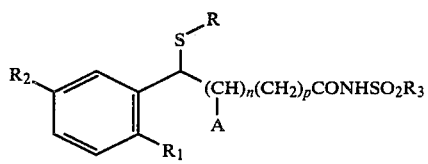

5. A compound of claim 4 which is N-[3-(carboxyethylthio)-3-[2-(8-phenyloctyl)phenyl]]propionylbenzenesulfonamide; and 6. A compound of claim 4 which is N-[3-(carboxyethylthio)-3-[2-(8-phenyloctyl)phenyl]]propionylmethanesulfonamide.

7. A pharmaceutical composition comprising a pharmaceutical carrier or diluent and a compound of claim 1.

8. The composition of claim 7 in a form suitable for administration orally, parenterally, topically, or by inhalation.

9. The composition of claim 7 in which the active component is 2-hydroxy-3-[2-(N-phenylsulfonylcarbamoylethyl)thiol-3-[2-(8-phenyloctyl)phenyl]-propanoic acid.

10. The composition of claim 7 in which the active component is N-[3-(carboxyethylthio)-3-[2-(8-phenyloctyl)phenyl]propionylbenzenesulfonamide.

11. The composition of claim 7 in which the active component is N-[3-(carboxyethylthio)-3-[2-(8-phenyloctyl)phenyl]propionylmethanesulfonamide.

12. A pharmaceutical composition comprising a pharmaceutical carrier or diluent and a compound of claim 1 and an histamine $H_1$-receptor antagonist.

13. A method of treating a disease in which antagonizing leukotriene activity is useful, which method comprises administering to a subject in need thereof an effective amount of the composition of claim 7.

14. A method for inhibiting antigen-induced respiratory anaphylaxis comprising administering an effective amount of a compound of claim 1 alone or in combination with a pharmaceutically acceptable carrier or diluent.

* * * * *

UNITED STATES PATENT AND TRADEMARK OFFICE
CERTIFICATE OF CORRECTION

PATENT NO. : 4,954,513

DATED : Sep. 4, 1990

INVENTOR(S) : Gleason, et al.

It is certified that error appears in the above-identified patent and that said Letters Patent is hereby corrected as shown below:

Title Page:

item [73]: "Beccham" should be -- Beecham --

Column 1, line 8: "SRS A" should be -- SRS-A --

Column 1, line 10: "SRS A" should be -- SRS-A --

Column 1, line 41: "($LTB_4$) Leukotrienes" should be -- ($LTB_4$). Leukotrienes --

Column 2, line 60: "Ford Hutchinson," should be -- Ford-Hutchinson, --

Column 7, line 9: "$C_{8-13}$alkyl $C_{7-12}$alkoxy," should be -- $C_{8-13}$alkyl, $C_{7-12}$alkoxy --

Column 7, line 29: "2 hydroxy 3 [2 (N phenylsulfonylcarbamoylethyl)" should be -- 2-hydroxy-3-[2-(N-phenylsulfonylcarbamoylethyl) --

Column 7, line 30: "thio]3 [2 (phenyloctyl)phenyl]propanoic" should be -- thio]-3-[2-(phenyloctyl)phenyl]propanoic --

Column 7, line 45: "N [3 (carboxyethylthio)-3 [2-(8-phenyloctyl-" should be -- N-[3-(carboxyethylthio)-3-[2-(8-phenyloctyl)- --

Column 7, line 47: "N [3 (carboxyethylthio) 3-[2 (8 phenyloctyl)" should be -- N-[3-(carboxyethylthio)-3-[2-(8-phenyloctyl) --

Column 7, line 65: "alkyl or" should be -- alkyl- or --

Column 8, line 33: "2 hydrox-" should be -- 2-hydrox- --

Column 8, line 34: "2 chloro-" should be -- 2-chloro- --

Column 8, line 37: "alkyl or" should be -- alkyl- or --

UNITED STATES PATENT AND TRADEMARK OFFICE
CERTIFICATE OF CORRECTION

PATENT NO. : 4,954,513

DATED : Sep. 4, 1990

INVENTOR(S) : Gleason, et al.

It is certified that error appears in the above-identified patent and that said Letters Patent is hereby corrected as shown below:

Column 8, line 67: "3 hydroxypropanoate" should be -- 3-hydroxypropanoate --

Column 9, line 3: "3 hydroxypropanoate" should be -- 3-hydroxypropanoate --

Column 9, line 4: "2 bromopropanoate" should be -- 2-bromopropanoate --

Column 9, line 11: "compounds Of" should be -- compounds of --

Column 9, line 50: "$CH(OH)(CH_2)_pCOHHSO_2R_3$" should be -- $CH(OH)(CH_2)_pCONHSO_2R_3$ --

Column 10, line 9: "of t following" should be -- of the following --

Column 11, line 66: "cross sectional" should be -- cross-sectional --

Column 12, line 15: "concentration response" should be -- concentration-response --

Column 14, line 10: "antigen induced" should be -- antigen-induced --

Column 14, line 13: "2-[4-(5-bromo 3-" should be -- 2-[4-(5-bromo-3- --

Column 14, line 14: "methylpyrid-2-yl)butylamino]-5-[6-methyl-pyrid 3-" should be -- methylpyrid-2-yl)butylamino]-5-[(6-methyl-pyrid-3- --

Column 14, line 42: "8 phenyloctanoic" should be -- 8-phenyloctanoic --

Column 15, line 38: "hexamethylpho-sphoramine" should be -- hexamethylphosphoramide --

Column 15, line 40: "5 hexynyl" should be -- 5-hexynyl --

UNITED STATES PATENT AND TRADEMARK OFFICE
CERTIFICATE OF CORRECTION

PATENT NO. : 4,954,513

DATED : Sep. 4, 1990

INVENTOR(S) : Gleason, et al.

It is certified that error appears in the above-identified patent and that said Letters Patent is hereby corrected as shown below:

Column 15, line 46: "qive 1 phenylocta-1,7-diyne." should be -- give 1-phenylocta-1,7-diyne. --

Column 15, line 58: "(24 1 mmoles)" should be -- (24.1 mmoles) --

Column 15, line 67: "to 60°" should be -- to -60° --

Column 16, line 7: "at 20° C." should be -- at -20° C. --

Column 16, line 37: "acetate formic" should be -- acetate-formic --

Column 16, line 44: "N-[3-(carboxyethylthio)-3-[2 (8" should be -- N-[3-(carboxyethylthio)-3-[2-(8 --

Column 16, line 46: "3-[(2-Carbomethoxyethyl)thio]-3-[2-(8 phenyloc-" should be -- 3-[(2-Carbomethoxyethyl)thio]-3-[2-(8-phenyloc- --

Column 16, line 50: "4 dimethylaminopyridine" should be -- 4-dimethylaminopyridine --

Column 17, line 3: "N-[3-(carboxyethylthio)-3-[2 (8" should be -- N-[3-(carboxyethylthio)-3-[2-(8- --

Column 17, line 6: "3-[(2 Carbomethoxyethyl)thio]-3-[2-(8 phenyloctyl)" should be -- 3-[(2-Carbomethoxyethyl)thio]-3-[2-(8-phenyloctyl) --

Column 17, line 35: "-[2-(N-phenylsulfonylcarbamoylethyl)thio]-3-[2-(8" should be -- -[2-(N-phenylsulfonylcarbamoylethyl)thio]-3-[2-(8- --

Column 17, line 38: "3-[2-(8" should be -- 3-[2-(8- --

Column 18, line 20: "2-t" should be -- 2-t- --

UNITED STATES PATENT AND TRADEMARK OFFICE
CERTIFICATE OF CORRECTION

PATENT NO. : 4,954,513

DATED : Sep. 4, 1990

INVENTOR(S) : Gleason, et al.

It is certified that error appears in the above-identified patent and that said Letters Patent is hereby corrected as shown below:

Column 18, line 52: "4-dimethyl aminopy-" should be -- 4-dimethylaminopy- --

Column 19, line 11: "2-(2-methoxyphenyl) 4,4-dimethyloxazo-" should be -- 2-(2-methoxyphenyl)-4,4-dimethyloxazo --

Column 20, line 37: "chromatoqraphed" should be -- chromatographed --

Column 20, line 50: New paragraph beginning: -- The compound of .... --

Column 20, line 55: "3-[2--" should be -- 3-[2- --

Column 20, line 67: "chromatographedusing" should be -- chromatographed using --

Column 21, line 18: "chromatographedwith" should be -- chromatographed with --

Column 21, line 35: "2-methyl 3-hydroxy-3-(2-dodecylphenyl)" should be -- 2-methyl-3-hydroxy-3-(2-dodecylphenyl) --

Column 21, line 41: "ice methanol" should be -- ice-methanol --

Column 21, line 59: "chromatographedon" should be -- chromatographed on --

Column 21, line 66: "67:" should be -- $\delta$: --

Column 22, line 27: "2 bromo 5-trifluoromethyl" should be -- 2-bromo-5-trifluoromethyl --

UNITED STATES PATENT AND TRADEMARK OFFICE
CERTIFICATE OF CORRECTION

PATENT NO. : 4,954,513

DATED : Sep. 4, 1990

INVENTOR(S) : Gleason, et al.

It is certified that error appears in the above-identified patent and that said Letters Patent is hereby corrected as shown below:

Column 22, line 29: "1 phenylocta-1," should be -- 1-phenylocta-1, --

Column 22, line 39: "2 (8-phenyloc-" should be -- 2-(8-phenyloc- --

Column 23, line 1: "chromatoqraphed" should be -- chromatographed --

Column 23, line 30: "qive" should be -- give --

Column 23, line 58: "(2.94 q," should be -- (2.94 g, --

Column 24, line 5: "(1.2 q," should be -- (1.2 g, --

Column 24, line 14: "qive" should be -- give --

Column 24, line 36: "chromatoqraphed" should be -- chromatographed --

Column 24, line 37: "qive" should be -- give --

Column 24, line 46: "qaseous" should be -- gaseous --

Column 24, line 47: "resultinq" should be -- resulting --

Column 24, line 52: "maq-" should be -- mag- --

Column 25, line 1: "2-Hydroxy-3-[4-(N methylsulfonyl-" should be -- 2-Hydroxy-3-[4-(N-methylsulfonyl- --

Column 25, line 11: "(644 mq," should be -- (644 mg, --

UNITED STATES PATENT AND TRADEMARK OFFICE
CERTIFICATE OF CORRECTION

PATENT NO. : 4,954,513

DATED : Sep. 4, 1990

INVENTOR(S) : Gleason, et al.

It is certified that error appears in the above-identified patent and that said Letters Patent is hereby corrected as shown below:

Column 25, line 12: "(325 mq," should be -- (325 mg, --

Column 25, line 22: "qaseous" should be -- gaseous --

Signed and Sealed this

Eighth Day of September, 1992

Attest:

DOUGLAS B. COMER

*Attesting Officer*   *Acting Commissioner of Patents and Trademarks*